(12) United States Patent
Elian et al.

(10) Patent No.: US 9,536,953 B2
(45) Date of Patent: Jan. 3, 2017

(54) METHOD FOR MAKING A SENSOR DEVICE USING A GRAPHENE LAYER

(71) Applicant: Infineon Technologies AG, Neubiberg (DE)

(72) Inventors: Klaus Elian, Alteglofsheim (DE); Guenther Ruhl, Regensburg (DE); Horst Theuss, Wenzenbach (DE); Irmgard Escher-Poeppel, Duggendorf (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 14/745,428

(22) Filed: Jun. 20, 2015

(65) Prior Publication Data

US 2015/0287788 A1 Oct. 8, 2015

Related U.S. Application Data

(60) Continuation of application No. 14/289,512, filed on May 28, 2014, now Pat. No. 9,070,615, which is a (Continued)

(51) Int. Cl.
*H01L 29/06* (2006.01)
*H01L 29/16* (2006.01)
(Continued)

(52) U.S. Cl.
CPC ......... *H01L 29/1606* (2013.01); *G01N 27/127* (2013.01); *H01L 21/561* (2013.01); *H01L 23/28* (2013.01); *H01L 23/293* (2013.01); *H01L 23/315* (2013.01); *H01L 23/3135* (2013.01); *H01L 23/49562* (2013.01); *H01L 24/49* (2013.01); *G01N 33/0059* (2013.01);

*H01L 21/568* (2013.01); *H01L 24/13* (2013.01); *H01L 24/16* (2013.01); *H01L 24/24* (2013.01); *H01L 24/48* (2013.01); *H01L 24/94* (2013.01); *H01L 24/96* (2013.01); *H01L 2224/02379* (2013.01); *H01L 2224/0346* (2013.01); *H01L 2224/0401* (2013.01); *H01L 2224/04042* (2013.01); *H01L 2224/05548* (2013.01); *H01L 2224/12105* (2013.01); *H01L 2224/13022* (2013.01); *H01L 2224/13024* (2013.01); *H01L 2224/13111* (2013.01); *H01L 2224/16225* (2013.01); *H01L 2224/16227* (2013.01);

(Continued)

(58) Field of Classification Search
CPC .......................... H01L 29/1606; G01N 27/127
USPC .............................................................. 257/9
See application file for complete search history.

(56) References Cited

U.S. PATENT DOCUMENTS 5,401,376 A 3/1995 Foos et al.
6,300,169 B1 10/2001 Weiblen et al.
(Continued)

OTHER PUBLICATIONS

Fowler, J. D., et al., "Practical Chemical Sensors from Chemically Derived Graphene," ACS NANO, downloaded from http://pubs.acs.org on Mar. 10, 2009, pp. 301-306, vol. 3, No. 2, ACS Publications.
(Continued)

*Primary Examiner* — David S Blum
(74) *Attorney, Agent, or Firm* — Slater Matsil, LLP

(57) ABSTRACT

A graphene layer is generated on a substrate. A plastic material is deposited on the graphene layer to at least partially cover the graphene layer. The substrate is separated into at least two substrate pieces.

29 Claims, 11 Drawing Sheets

Related U.S. Application Data division of application No. 13/226,173, filed on Sep. 6, 2011, now Pat. No. 8,759,153.

(51) Int. Cl.

| | | |
|---|---|---|
| *G01N 27/12* | (2006.01) | |
| *H01L 23/29* | (2006.01) | |
| *H01L 23/31* | (2006.01) | |
| *H01L 21/56* | (2006.01) | |
| *H01L 23/28* | (2006.01) | |
| *H01L 23/495* | (2006.01) | |
| *H01L 23/00* | (2006.01) | |
| *G01N 33/00* | (2006.01) | |

(52) U.S. Cl.
CPC ............ *H01L 2224/24011* (2013.01); *H01L 2224/24105* (2013.01); *H01L 2224/24226* (2013.01); *H01L 2224/48245* (2013.01); *H01L 2224/48247* (2013.01); *H01L 2224/48465* (2013.01); *H01L 2224/94* (2013.01); *H01L 2224/96* (2013.01); *H01L 2924/00014* (2013.01); *H01L 2924/12042* (2013.01); *H01L 2924/181* (2013.01); *H01L 2924/1815* (2013.01)

(56) References Cited

U.S. PATENT DOCUMENTS

| | | |
|---|---|---|
| 7,015,142 B2 | 3/2006 | DeHeer et al. |
| 7,134,198 B2 | 11/2006 | Nakatani et al. |
| 7,200,924 B2 | 4/2007 | Masuko |
| 7,732,859 B2 | 6/2010 | Anderson et al. |
| 7,803,660 B2 | 9/2010 | Murakami et al. |
| 8,080,441 B2 | 12/2011 | Suvorov |
| 2003/0205797 A1 | 11/2003 | Takahashi et al. |
| 2004/0040740 A1 | 3/2004 | Nakatani et al. |
| 2004/0055805 A1 | 3/2004 | Lich et al. |
| 2008/0017507 A1 | 1/2008 | Ramamurthy et al. |
| 2008/0136009 A1 | 6/2008 | Theuss et al. |
| 2008/0230920 A1 | 9/2008 | Behrens |
| 2009/0051052 A1 | 2/2009 | Yoshioka et al. |
| 2009/0236608 A1 | 9/2009 | De Heer et al. |
| 2010/0025660 A1 | 2/2010 | Jain et al. |
| 2010/0327847 A1 | 12/2010 | Leiber et al. |
| 2011/0016981 A1 | 1/2011 | Gebauer et al. |
| 2011/0095342 A1 | 4/2011 | Daniel et al. |
| 2011/0101309 A1 | 5/2011 | Lin et al. |
| 2011/0210314 A1 | 9/2011 | Chung et al. |
| 2011/0227043 A1 | 9/2011 | Guo et al. |
| 2011/0291068 A1 | 12/2011 | Kobayashi |
| 2011/0298066 A1 | 12/2011 | Kim et al. |
| 2011/0309336 A1 | 12/2011 | Shin et al. |
| 2011/0315956 A1 | 12/2011 | Tischler et al. |
| 2012/0003438 A1 | 1/2012 | Appleton et al. |
| 2012/0206012 A1 | 8/2012 | Rosenblatt et al. |
| 2012/0212242 A1 | 8/2012 | Masel et al. |
| 2012/0217147 A1 | 8/2012 | Porter et al. |
| 2012/0255860 A1 | 10/2012 | Briman et al. |

OTHER PUBLICATIONS

Mohanty, N., et al., "Graphene-Based Single-Bacterium Resolution Biodevice and DNA Transistor: Interfacing Graphene Derivatives with Nanoscale and Microscale Biocomponents," NANO Letters, 2008, pp. 4469-4476, vol. 8, No. 12, American Chemical Society.

Robinson, J. T., et al., "Reduced Graphene Oxide Molecular Sensors," NANO Letters, 2008, pp. 3137-3140, vol. 8, No. 10, American Chemical Society.

Schedin, F., et al., "Detection of Individual Gas Molecules Adsorbed on Graphene," Nature Materials, 2007, vol. 6, 11 pages.

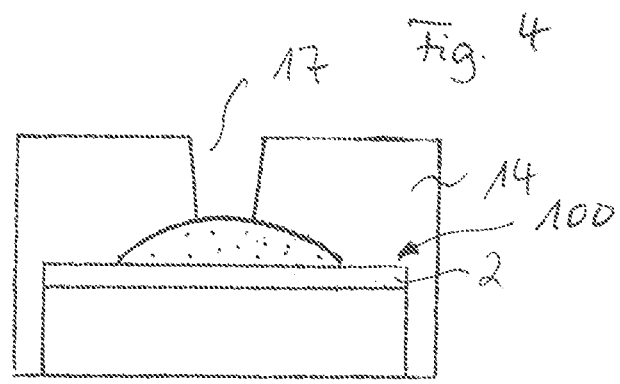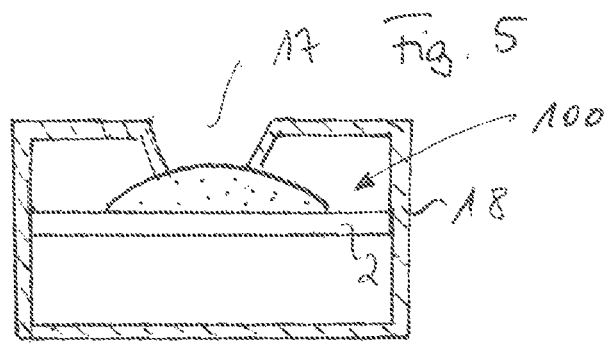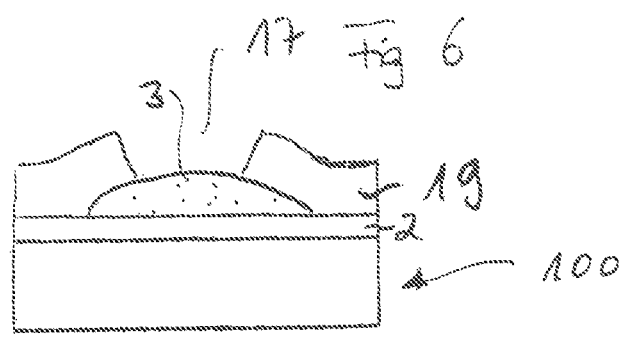

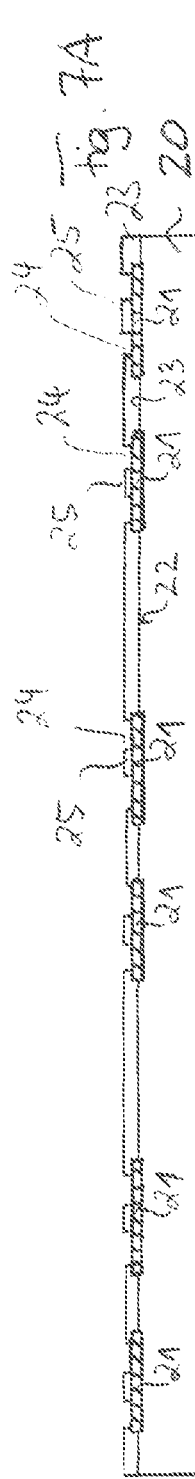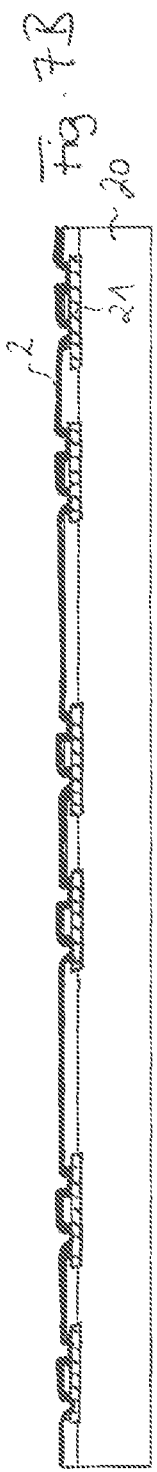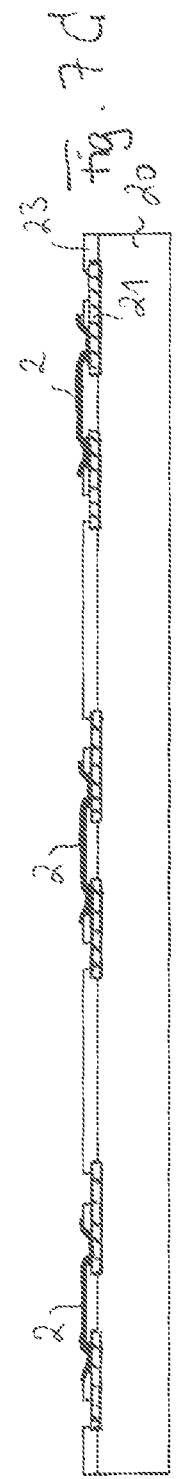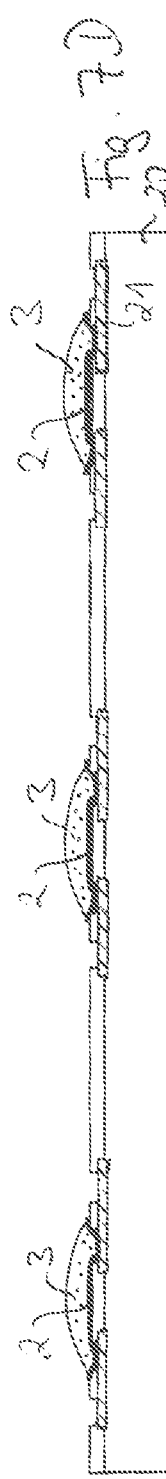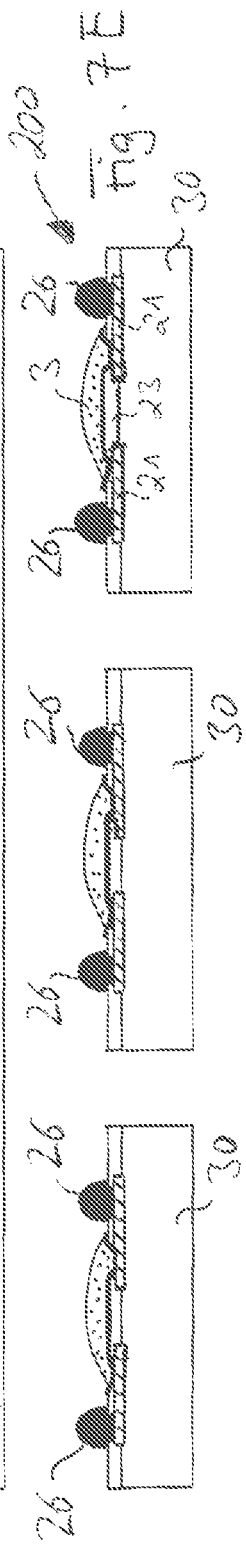

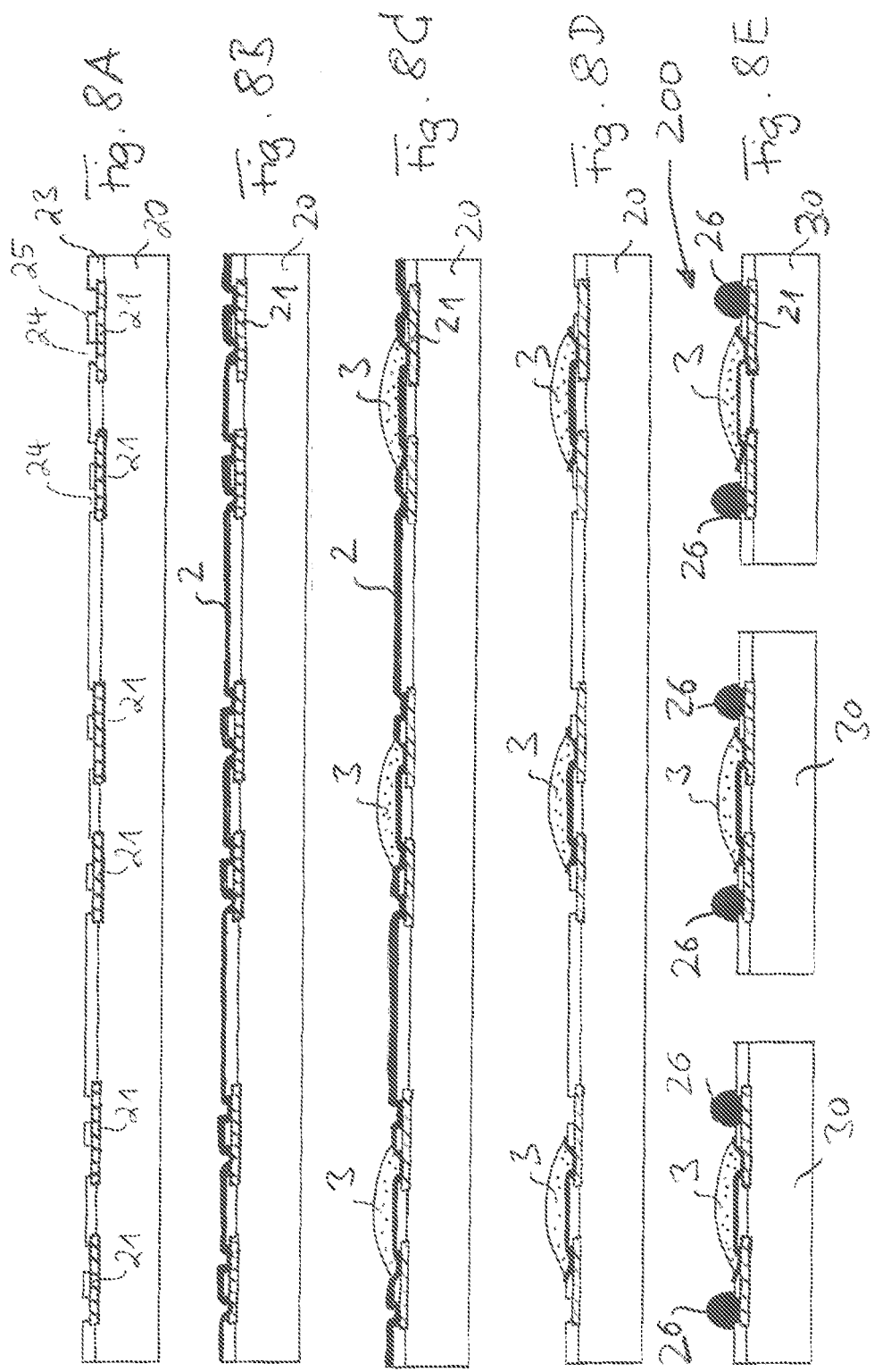

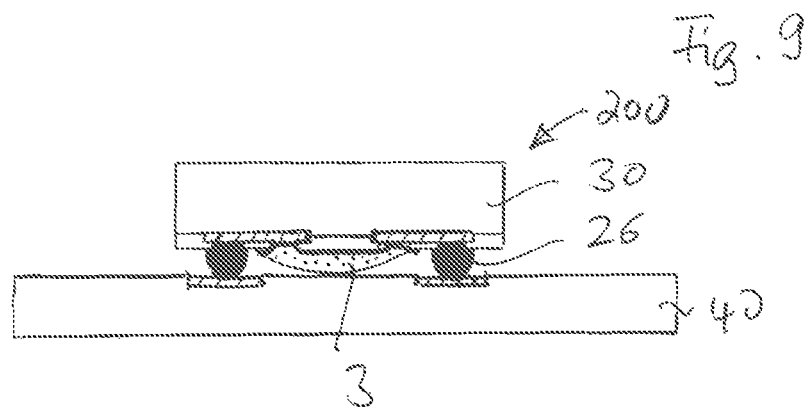
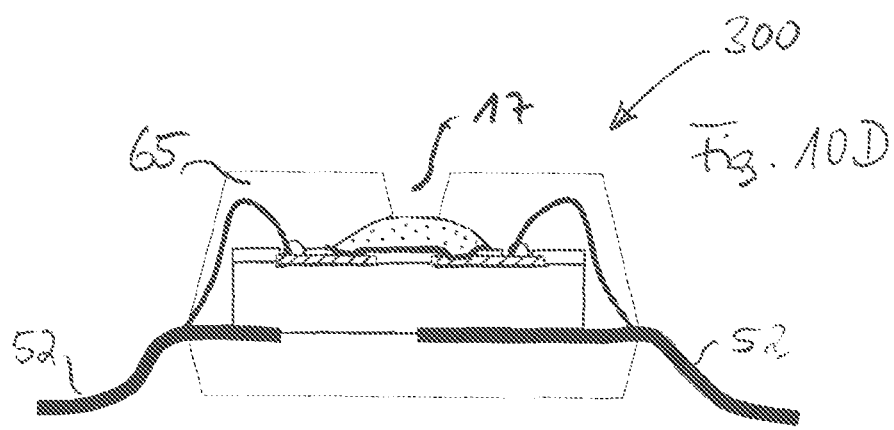
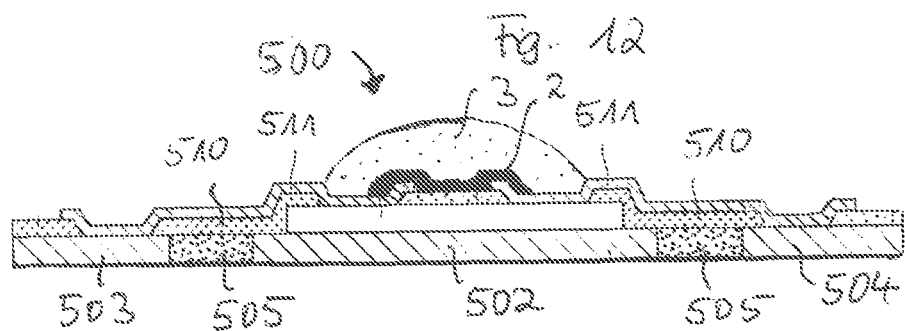

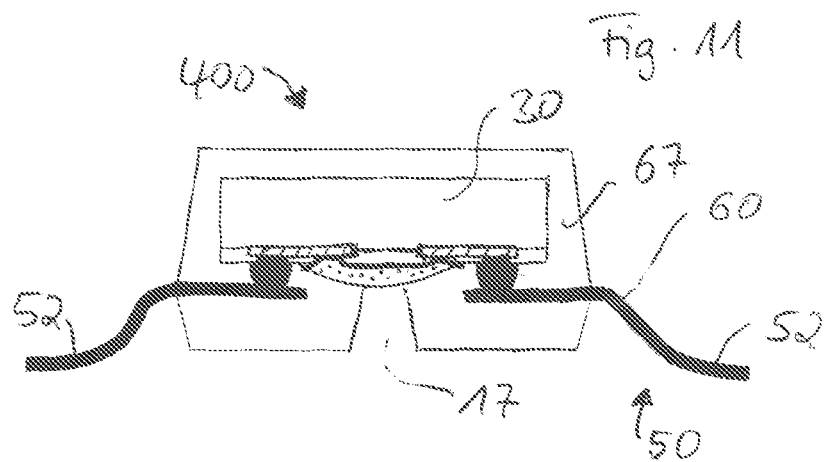
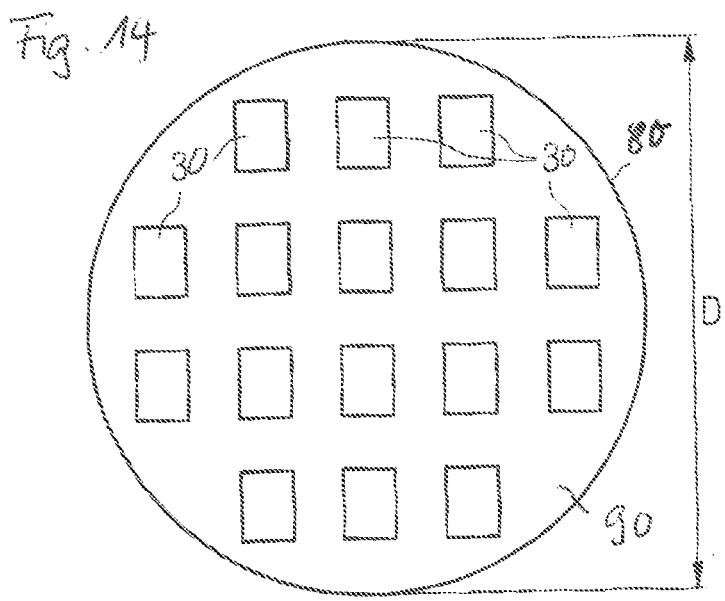
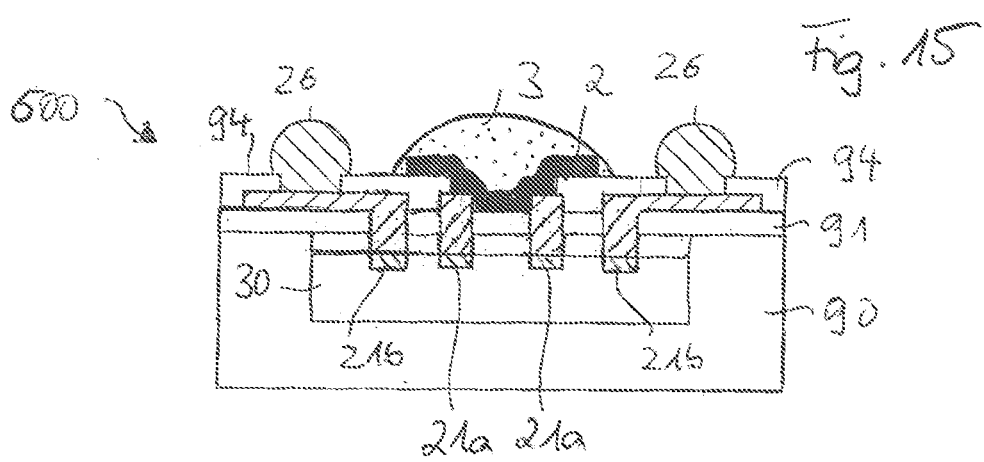

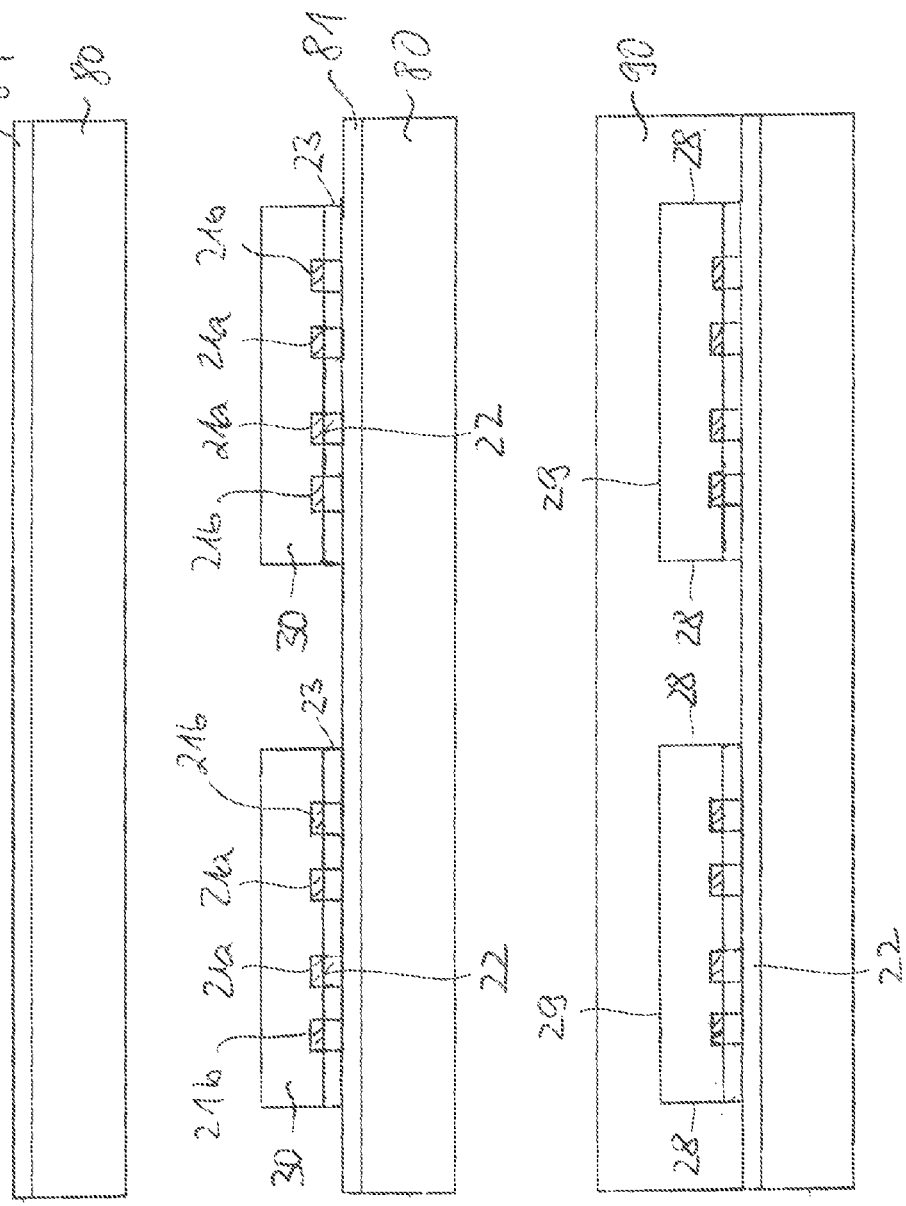

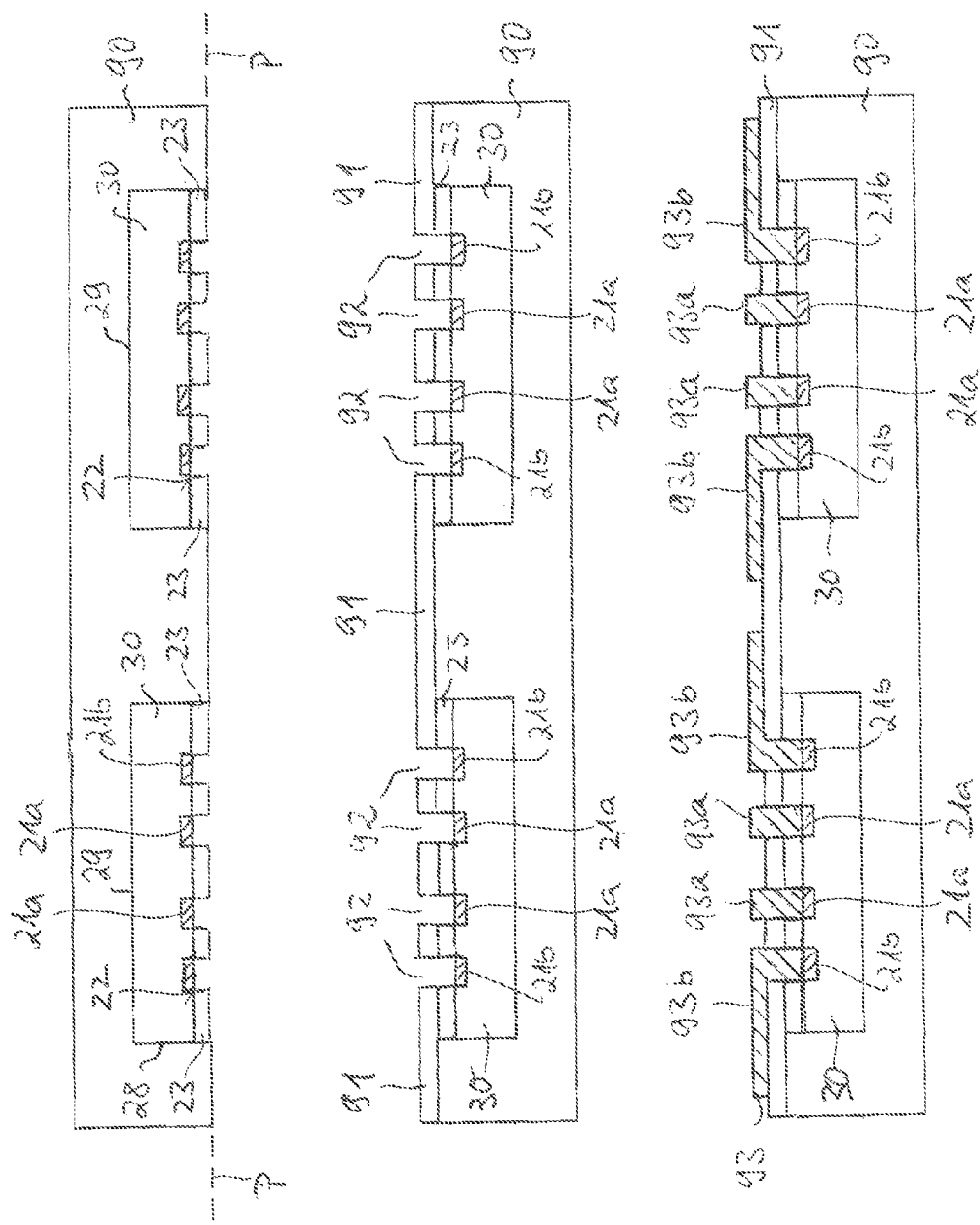

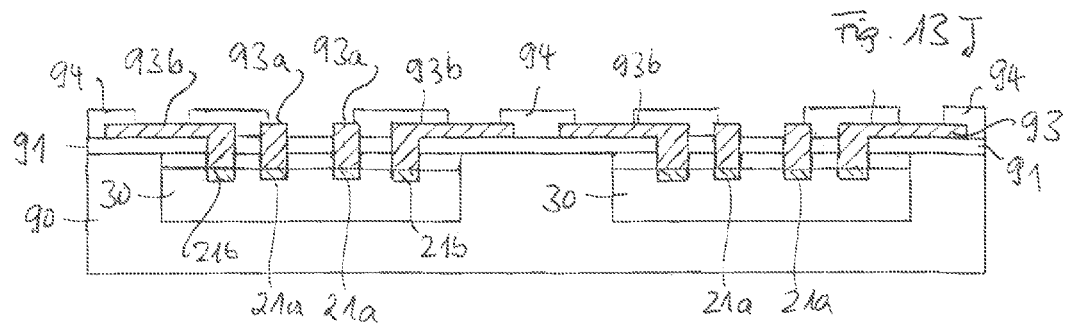
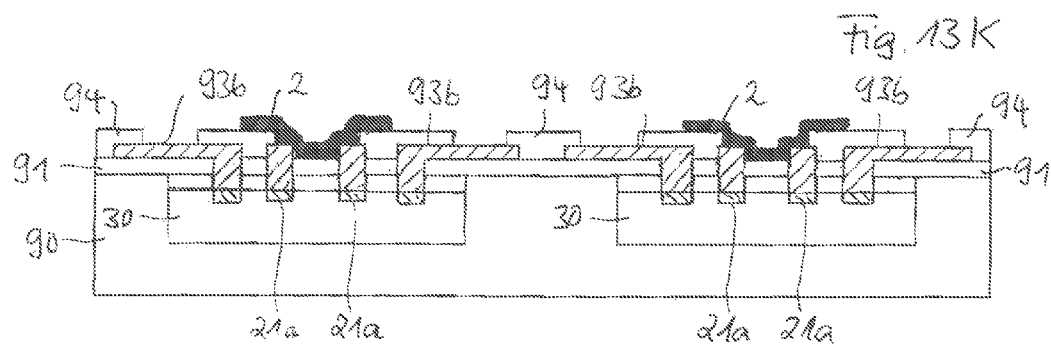
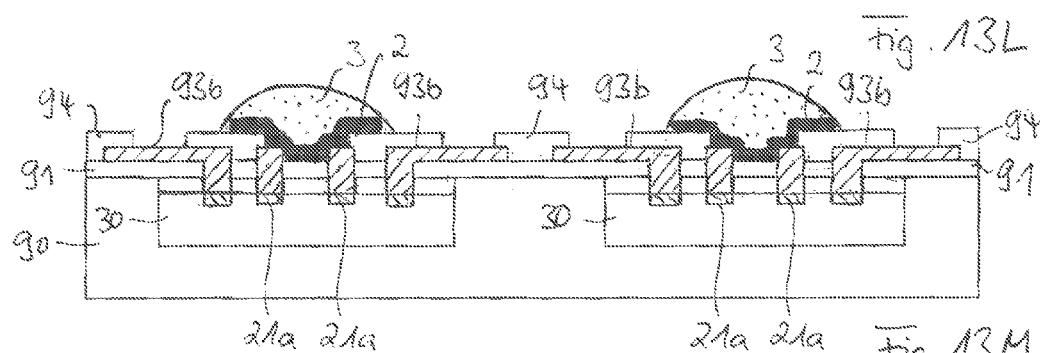
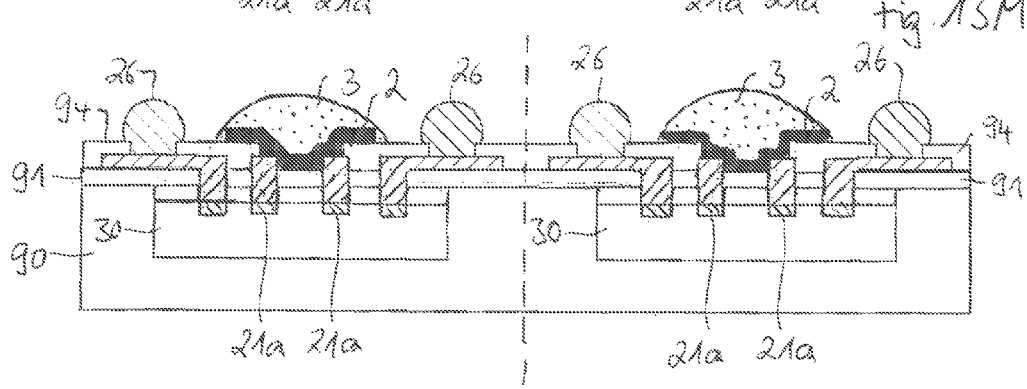

METHOD FOR MAKING A SENSOR DEVICE USING A GRAPHENE LAYER

This is a continuation application of U.S. application Ser. No. 14/289,512, issued on Jun. 30, 2015 as U.S. Pat. No. 9,070,615, entitled "Method for Making a Sensor Device Using a Graphene Layer" which was filed on May 28, 2014 which is a divisional application of U.S. application Ser. No. 13/226,173, issued on Jun. 24, 2014 as U.S. Pat. No. 8,759,153, entitled "Method for Making a Sensor Device Using a Graphene Layer" which was filed on Sep. 6, 2011, both of which applications are incorporated herein by reference.

TECHNICAL FIELD

This invention relates to an electronic device including a sensor, and in particular, to an electronic device including a fluid, chemical or biocomponent sensor.

BACKGROUND

In the development of devices including sensors special requirements may be taken into account, in particular, when designing the sensitivity and the package of a sensor device. For example, certain sensors, such as fluid, chemical or biocomponent sensors, may require an opening through which the substance which is to be detected is applied to the sensor. Such packages may become large, sophisticated and expensive. However, both the manufacturers and the consumers of electronic devices desire devices that are inexpensive, reduced in size and yet have increased device functionality.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 schematically illustrates a cross-sectional view of one embodiment of a sensor device;

FIG. 5 schematically illustrates a cross-sectional view of one embodiment of a sensor device;

FIG. 6 schematically illustrates a cross-sectional view of one embodiment of a sensor device;

FIGS. 7A to 7E schematically illustrate cross-sectional views of one embodiment of a method to produce a sensor device;

FIGS. 8A to 8E schematically illustrate cross-sectional views of one embodiment of a method to produce a sensor device;

FIG. 9 schematically illustrates a cross-sectional view of one embodiment of a sensor device;

FIGS. 10A to 10D schematically illustrate cross-sectional views of one embodiment of a method to produce a sensor device;

FIG. 11 schematically illustrates a cross-sectional view of one embodiment of a sensor device;

FIG. 12 schematically illustrates a cross-sectional view of one embodiment of a sensor device;

FIGS. 13A to 13M schematically illustrate cross-sectional views of one embodiment of a method to produce a sensor device;

FIG. 14 schematically illustrates a top view of the structure illustrated in FIG. 13G; and FIG. 15 schematically illustrates a cross-sectional view of one embodiment of a sensor device.

DETAILED DESCRIPTION OF ILLUSTRATIVE EMBODIMENTS

Figure 1A:
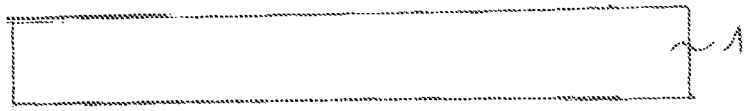
FIGS. 1A to 1C schematically illustrate cross-sectional views of one embodiment of a method.

In the following detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the figures being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

As employed in this Specification, the terms "coupled" and/or "electrically coupled" are not meant to mean that the elements must be directly coupled together; intervening elements may be provided between the "coupled" or "electrically coupled" elements.

Embodiments of devices which may contain semiconductor chips are described below. The semiconductor chips may be of different types, may be manufactured by different technologies and may include, for example, integrated electrical, electro-optical or electro-mechanical circuits and/or passives. The semiconductor chips may, for example, be designed as logic integrated circuits, analog integrated circuits, mixed signal integrated circuits, memory circuits or integrated passives. They may include control circuits, microprocessors or microelectro-mechanical components. The semiconductor chips need not be manufactured from specific semiconductor material, for example, Si, SiC, SiGe, GaAs, AlGaAs and, furthermore, may contain inorganic and/or organic materials that are not semiconductors, such as, for example, insulators, plastics or metals.

The sensor devices described below may include external contact elements such as, e.g., leads or solder deposits or contact pads on a package. The external contact elements may represent the external terminals of the package. They may be accessible from outside the package and may thus allow electrical contact to be made with the device from outside the package. Furthermore, the external contact elements may be thermally conductive and may serve as heat sinks for dissipating the heat generated by the semiconductor chip or chips embedded in the semiconductor package.

The external contact elements may be composed of any desired electrically conductive material, for example, of a metal, such as copper, aluminum or gold, a metal alloy or an electrically conductive organic material. Solder deposits, such as solder balls or solder bumps, may represent the external contact elements or may be deposited on the external contact elements.

The sensor devices may comprise an encapsulating material to form an encapsulation body (e.g., a molded body), which may be electrically insulating. The encapsulating material may be a dielectric material and may be made of any appropriate duroplastic, thermoplastic or thermosetting material or laminate (prepreg). The encapsulating material may contain filler materials. After its deposition, the encapsulating material may be only partially hardened and may be completely hardened after application of energy (e.g., heat, UV light, etc.) to form an encapsulation body. Various techniques may be employed to cover the semiconductor chips with the encapsulation body, for example, compression molding, injection molding, powder molding, liquid molding, dispensing or laminating.

In one embodiment, the encapsulation body may be used to produce so-called fan-out type packages. In a fan-out type package at least some of the external contact pads and/or conductor traces connecting the semiconductor chip to the external contact pads are located laterally outside of the outline of the semiconductor chip or do at least intersect the outline of the semiconductor chip. Thus, in fan-out type packages, a peripherally outer part of the package of the semiconductor chip is typically (additionally) used for electrically bonding the package to external applications, such as, e.g., application boards or, in stacked package applications, another package. This outer part of the package encompassing the semiconductor chip effectively enlarges the contact area of the package in relation to the footprint of the semiconductor chip, thus leading to relaxed constraints in view of package pad size and pitch with regard to later processing, e.g., second level assembly.

A graphene layer is generated on a substrate (e.g., wafer or artificial wafer or other carrier). The graphene layer may be applied on the substrate before separating the substrate into individual devices. By way of example, if the substrate is a wafer, the graphene layer may be generated on the wafer during wafer level processing, that is during frontend processing.

The graphene layer may be applied by a spin coating process. Further, the graphene layer may be applied by micro-mechanical cleavage of graphite or by a CVD (Chemical Vapor Deposition) process. By way of example, spin-coated graphene films may be produced by chemical oxidation and exfoliation of graphite to produce graphite oxide, its subsequent reduction to graphene by using, e.g., liquid anhydrous hydrazine as a reducing agent and solvent for dispersion of large, high quality graphene flakes, and by depositing this material using a centrifuged solution to achieve well dispersed, single layer graphene flakes.

Figure 1B:
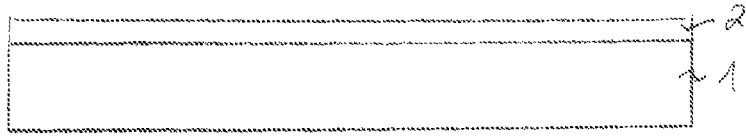
Figure 1C:
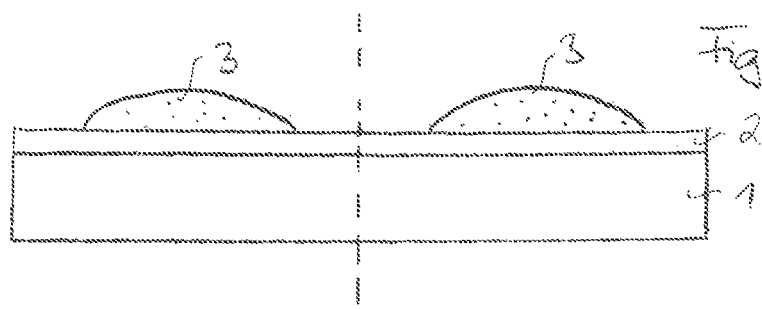
Figure 2:
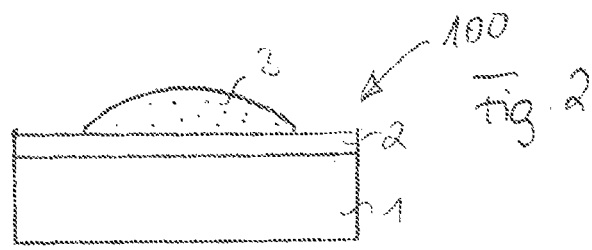
FIG. 2 schematically illustrates a cross-sectional view of one embodiment of a sensor device.

FIGS. 1A to 1C schematically illustrate one embodiment of a method to generate a sensor device 100 as shown in FIG. 2. According to FIG. 1A, a substrate 1 is provided. The substrate 1 may have the form of a plate. It may be made of different kinds of material. By way of example, the substrate 1 may be a semiconductor wafer, a so-called artificial wafer or a plate made of plastics such as, e.g., polyimide.

A graphene layer 2 is deposited on one main surface of the substrate 1. In one embodiment the graphene layer 2 may be an unstructured layer which may completely cover the respective main surface of the substrate 1. In another embodiment the graphene layer 2 may be generated as a structured layer which only partly covers the respective main surface of the substrate 1.

A plastic material 3 is deposited over the graphene layer 2 (FIG. 1C). The plastic material 3 may completely or partially cover the graphene layer 2. In one embodiment, the plastic material 3 may be deposited in a pre-structured, patterned form on the graphene layer 2 to only cover specific zones of the graphene layer 2. Further, in one embodiment, the plastic material 3 may be deposited as an unstructured, continuous layer and may then be structured to only cover specific zones of the graphene layer 2.

The plastic material 3 may be made of a material which selectively controls the exposure of the covered zone of the graphene layer 2 with substances of the environment. The selection of the plastic material 3 depends on the desired functionality of the sensor device to be fabricated. Depending on the selected plastic material 3 and its specificity to different substances, the sensor device will be sensitive to different substances.

By way of example, chemical sensors sensitive to specific elements or molecules such as, e.g., $CO_2$, $H_2O$, $NO_2$, $NH_3$, etc. may be provided. Further, biocomponent sensors sensitive to, e.g., DNA, microbes, specific cells, the content of oxygen in blood, etc., may be provided. Still further, fluid sensor devices such as, e.g., gas sensors or liquid sensors may be provided, e.g., to sense one or more of the substances mentioned above.

In one embodiment, the plastic material 3 may comprise polyethylenterephtalate. The permeability of polyethylenterephtalate against $CO_2$ is more than one order of magnitude greater than the permeability of polyethylenterephtalate against $O_2$, carbon hydrides or $H_2O$. That way, the selectivity of a $CO_2$ sensor may be significantly increased.

In one embodiment, the plastic material 3 may comprise polyvinylidene chloride. Polyvinylidene chloride may increase the sensitivity of a humidity sensor against $O_2$ and $CO_2$ by more than three orders of magnitude. Further, there are a great variety of other materials which provide different permeabilities and thus selectivities for various specific chemical elements, molecules, biocomponents or other substances.

In one embodiment (not illustrated in FIGS. 1A to 1C) the graphene layer 2 may be structured before depositing the plastic material 3 on the graphene layer 2.

In one embodiment (not shown in FIGS. 1A to 1C) the graphene layer 2 may be structured after depositing the plastic material 3 on the graphene layer 2 by using the deposited plastic material 3 as a mask. Both these possible processes of structuring the graphene layer 2 will be explained with reference to embodiments further below.

The plastic material 3, which is also referred to in the art as a glob top material, may be deposited on the graphene layer 2 by, e.g., a dispensing, printing or CVD process. In one embodiment the plastic material 3 is deposited in a pre-structured form on the graphene layer 2. By way of example, dispensing or printing processes are available to deposit structures such as, e.g., islands of plastic material 3 on the graphene layer 2. In one embodiment the plastic material 3 is deposited on the graphene layer 2 as an unstructured, continuous layer. In this embodiment, the structuring of the plastic material 3 on the graphene layer 2 may be provided by using photo-lithographic methods and/or etching methods.

As illustrated in FIG. 1C, sensor devices 100 are then separated from one another by separation of the substrate 1 and possibly the graphene layer 2 and the plastic material 3.

By way of example, sawing, cutting, etching or laser beams may be used for the separation step.

The operational principle of the graphene sensor devices described below is based on changes in their electrical conductivity (or resistance) due to substances absorbed on the surface of the graphene layer 2 extending below the plastic material 3. The electrical conductivity (or resistance) of the graphene layer 2 is highly sensitive to adsorbates, with the kind of adsorbates reaching the graphene's surface being controlled by the composition of the plastic material 3 as explained above. Further, the selectivity of graphene to different substances may be controlled by adjustable surface chemistry of the graphene layer 2. In this connection it is to be noted that the term graphene as used herein is to be understood in a broad meaning. In particular, it is intended that the term graphene may also comprise graphene-based layers with modifiable chemical functionality such as graphene derivatives and/or so-called chemically modified graphenes.

Figure 3A:
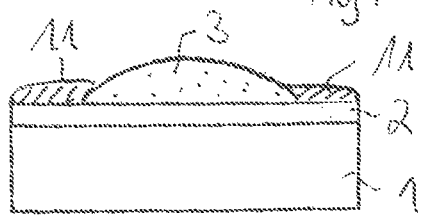
FIGS. 3A and 3B schematically illustrate cross-sectional views of embodiments of a sensor device.
Figure 3B:
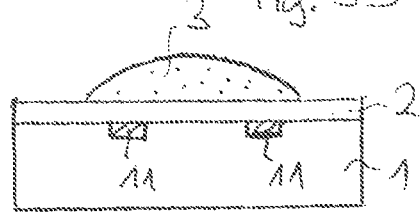

The changes in electrical conductivity or resistance of the graphene layer 2 covered by the plastic material 3 may be sensed by at least two electrical contacts applied to the graphene layer 3. By way of example, FIGS. 3A and 3B illustrate two electrical contacts 11 applied to the graphene layer 2, with the electrical contacts 11 being arranged in a spaced apart relationship. In one embodiment (FIG. 3A) the electrical contacts 11 are deposited on the upper surface of the graphene layer 2. In one embodiment (FIG. 3B) the electrical contacts 11 are provided to connect to the lower surface of the graphene layer 2. In both embodiments, the electrical contacts 11 are located such that the length of the graphene layer 2 in between the electrical contacts 11 is completely covered by the diffusion-selective plastic material 3. The principles illustrated in the embodiments of FIGS. 3A and 3B are applicable to other embodiments described herein.

FIG. 4 illustrates a cross-sectional view of one embodiment of a sensor device. In this embodiment, the sensor device 100 is encapsulated in an encapsulation body 14. The encapsulation body 14 has an opening 17 to expose the plastic material 3 to the environment.

As will be explained further below in greater detail, the encapsulation body 14 may be fabricated by way of molding (for example, compression molding, injection molding, granulate molding, powder molding or liquid molding). Typically, in a molding process a lower mold half and an upper mold half are used to define a cavity in which the encapsulation body 14 is formed.

In one embodiment the opening 17 to expose the plastic material 3 is formed during the molding process. By way of example, the upper mold half may be provided with a dome or post protruding into the mold cavity and pressing onto the upper surface of the plastic material 3. That way the opening 17 may be recessed by the dome of the molding tool. In another embodiment the opening 17 may be generated after the molding process and the formation of the encapsulation body 14 by machining, e.g., by mechanical or laser drilling or milling.

FIG. 5 illustrates a cross-sectional view of one embodiment of a sensor device. In this sensor device the sensor device 100 is accommodated in a hollow housing 18 made of, e.g., plastic. Similar to the embodiment illustrated in FIG. 4, the hollow housing 18 has an opening 17 to expose a part of the upper surface of the plastic material 3. The walls of the opening 17 may tightly connect to the upper surface of the plastic material 3 in order to avoid any substances of the environment to enter the space within the hollow housing 18.

FIG. 6 illustrates a cross-sectional view of one embodiment of a sensor device. In this embodiment the sensor device 100 is covered by a laminate material 19 encapsulating the upper surface of the sensor device 100. The laminate material may be a polymer foil having an opening 17. Again, similar to the embodiments illustrated in FIGS. 4 and 5, the opening 17 exposes a part of the surface of the plastic material 3.

In one embodiment the laminate material 19 may be laminated onto the structure shown in FIG. 1C before separating the substrate 1 into individual sensor devices 100. In this case the laminate material 19 may have a pattern of openings 17 aligned to the pattern of plastic material 3 and/or sensor devices 100 to be separated from the structure shown in FIG. 1C.

It is to be noted that in the embodiments of FIGS. 4 to 6 the sensor devices 100 may be equipped with electrical contacts 11 as illustrated in FIG. 3A and/or FIG. 3B.

The functionality of the sensor device 100 may significantly depend on the design of the substrate 1. If the substrate 1 comprises a semiconductor chip including an integrated circuit, the variations of the electric conductivity or resistance sensed by the electrical contacts 11 may directly be measured and, if desired, processed by the integrated circuit. To this end, the integrated circuit may comprise analog circuitry such as, e.g., a testing bridge, digital circuitry such as, e.g., logic circuitry, semiconductor memory, input/output circuitry, and/or mixed circuitry. Further, the substrate 1 may comprise a heater and/or a temperature receiving element and/or a control circuitry for controlling the heater in response to the output of the temperature receiving element. The heater, the temperature receiving element and the control circuitry may each be implemented in a semiconductor chip contained in the substrate 1 or off-chip.

In one embodiment the substrate 1 is a plastic plate as, for example, is used in a chip card or smart card. By way of example, the embodiment of FIG. 6 may illustrate a chip card or smart card designed as or containing a sensor device. In such a smart card or chip card the graphene layer 2 may either be deposited over the semiconductor chip (not illustrated) embedded in the plastic plate or may be deposited over the plastic plate as such, e.g., a polyimide plate. In the latter case conductor traces on the plastic plate or dielectric substrate may be used to electrically connect to the graphene layer 2. It is to be noted that it is also possible to use a plastic plate as substrate 1 without any semiconductor chip embedded therein. The conductivity of the graphene layer 2 may, in this case, be measured by external devices designed to make contact to external electrodes on the card which are coupled, e.g., by conductor traces to the graphene layer 2.

FIGS. 7A to 7E schematically illustrate a method for manufacturing a semiconductor device 200 as shown in FIG. 7E, or, if mounted on a board, in FIG. 9. The method illustrated in FIGS. 7A to 7E is an implementation of the method shown in FIGS. 1A to 1C. The details of the production method that are described below can therefore be likewise applied to the method illustrated in FIGS. 1A to 1C. Vice versa, the details described in conjunction with FIGS. 1A to 1C are likewise applicable to the method of FIGS. 7A to 7E. Furthermore, the semiconductor device 200 is an implementation of the semiconductor device 100. The details of the semiconductor device 200 that are described below can therefore be likewise applied to the semiconductor device 100, and vice versa.

In the embodiment shown in FIGS. 7A to 7E, the substrate 1 is a wafer 20 made of semiconductor material. The semiconductor wafer 20 may include a bulk silicon in which integrated circuits are embedded. Chip contact pads referred to in the following as chip electrodes 21 are located on a first main face 22 of the semiconductor wafer 20. The chip electrodes 21 correspond to the electrical contacts 11 of the embodiment shown in FIG. 3B. The integrated circuits embedded in the semiconductor wafer 20 can be electrically accessed via the chip electrodes 21. The chip electrodes 21 may be made of a metal, for example, aluminum or copper, and may have any desired shape and size. It is to be noted that the chip electrodes 21 illustrated in FIGS. 7A to 7E are chip electrodes intended to be coupled to a graphene layer 2 to sense the conductivity or resistance thereof. However, the semiconductor wafer 20 may be provided with other chip electrodes not shown in FIGS. 7B to 7E intended to be used, e.g., for power supply, I/O circuitry, heater, temperature receiving element, etc.

A structured insulating layer 23 may be generated on the first main face 22 of the semiconductor wafer 20 as illustrated in FIG. 7A. The insulating layer 23 may be fabricated in various ways. For example, the insulating layer 23 may be deposited from a gas phase or from a solution, or can be laminated onto the first main face 22. Furthermore, thin-film technology methods can be used for the application of the insulating layer 23. The insulating layer 23 may be fabricated from a polymer, such as parylene, photoresist material, imide, epoxy, duroplast, silicone. The thickness of the insulating layer 23 may be up to 10 µm or even higher. The insulating layer 23 may also be a hard passivation layer of, e.g., silicon dioxide, silicon nitride or of an inorganic, ceramic-like material, such as silicon-carbon compounds.

In order to electrically connect to the integrated circuits embedded in the semiconductor wafer 20, the insulating layer 23 may be opened in areas where the chip electrodes 21 are arranged as illustrated in FIG. 7A. The openings 24 in the insulating layer 23 may, for example, be produced by using photolithographic methods and/or etching methods. It is to be noted that lands, stripes or circles 25 of the insulating layer 23 may remain on at least some of the chip electrodes 21 and may, e.g., be located in a central part of the chip electrodes 21.

FIG. 7B illustrates the deposition of a graphene layer 2. The graphene layer 2 may be deposited as an unstructured, continuous layer at wafer level. Thus, the graphene layer 2 may be deposited on the insulating layer 23 and on the chip electrodes 21 exposed by the openings 24 of the insulating layer 23, and can make electrical contact to the chip electrodes 21. The deposition process of the graphene layer 2 may be identical or similar to one or more of processes described above with reference to other embodiments. Therefore, reiteration of the corresponding descriptions is omitted for the sake of brevity.

The graphene layer 2 may then be structured as shown in FIG. 7C. In one embodiment, a photoresist layer may be deposited, for example, spin-coated, on top of the graphene layer 2 (not illustrated). By exposure to light having a suitable wavelength through a mask and subsequent development, recesses are formed in the photoresist layer. Subsequently, if the photoresist material is of a positive tone, the portions of the graphene layer 2 that are exposed by the recesses may be removed by using an appropriate solvent or etching agent, e.g., by using an $O_2$ plasma etching method. If the photoresist material is of a negative tone, all not exposed areas are removed by the solvent or etching agent. The remaining portions of the graphene layer 2 may be continuous between each two chip electrodes 21 associated with each one of the integrated circuits embedded in the semiconductor wafer 20, and may have recesses elsewhere.

According to FIG. 7D, a plastic material 3 is deposited over the remaining portions of the graphene layer 2. This step corresponds to the process described in conjunction with FIG. 1C, and reference is made thereto in order to avoid reiteration. In one embodiment, the plastic material 3 may completely cover and hermetically seals the remaining portions of the graphene layer 2. In one embodiment, the plastic material 3 at least covers the remaining portions of the graphene layer 2 over the length where it extends between the chip electrodes 21. In both cases, substances of the environment adsorbing on the graphene layer 2 at a location between the two chip electrodes 21 have to penetrate the diffusion-selective plastic material 3.

As already mentioned in relation to other embodiments, the deposition of the plastic material 3 may be accomplished in a pre-structured manner, e.g., by dispensing or printing. If the plastic material 3 is deposited in a pre-structured manner, remaining parts of the insulating layer 23 may assist the deposition process. By way of example, if the plastic material 3 deposited on the semiconductor wafer 20 is a viscous liquid, the lands, stripes or circles 25 of the insulating layer 23 may act as barriers to prevent the liquid from distributing over the surface of the semiconductor wafer 20. That way, the lands, stripes or circles 25, together with the viscosity of the liquid plastic material 3, may guarantee a minimum height of, e.g., more than 10, 50 or even 100 µm of thickness of the plastic material 3 over the length where it extends between the chip electrodes 21. That way, the selectivity of the plastic material 3 may be improved or a minimum selectivity be set.

As illustrated in FIG. 7E, the semiconductor wafer 20 may then be singulated into individual semiconductor chips 30, for example, by sawing, cutting, etching or laser ablation, e.g., stealth dicing. Only three of these semiconductor chips 30 are illustrated in FIG. 7E. The semiconductor chip 30 illustrated in FIG. 7E may be one specific implementation of the piece of substrate 1 shown in FIG. 2.

Solder deposits 26 may be placed onto the chip electrodes 21 as illustrated in FIG. 7E. The solder deposits 26 may be applied to the chip electrodes 21 by so-called "ball placement", in which pre-shaped balls composed of solder material are applied to the chip electrodes 21. As an alternative to "ball placement", the solder deposits 26 may, for example, be applied by means of stencil printing with a solder paste, followed by a heat-treatment process. The solder material may be formed from metal alloys which are composed, for example, from the following materials: SnPb, SnAg, SnAgCu, SnAgCuNi, SnAu, SnCu and SnBi.

In one embodiment, the solder deposits 26 are applied on wafer level, i.e., prior to the step of singulating the semiconductor wafer 20 into individual semiconductor chips 30.

In one embodiment, the solder deposits 26 are applied on the individual semiconductor chips 30, i.e., after the step of singulating the semiconductor wafer 20 into semiconductor chips 30.

In one embodiment, the solder deposits 26 are attached to the chip electrodes 21 which make direct electrical contact to the graphene layer 2. This allows direct external access to the graphene layer 2. Additional solder deposits 26 may be attached to chip electrodes 21 which are not directly connected to the graphene layer 2 (not illustrated).

In one embodiment, the solder deposits 26 are attached only to chip electrodes 21 which do not make direct electrical contact to the graphene layer 2 (not illustrated). In this case, in particular, the integrated circuit formed in the semiconductor chip 30 typically comprises a sensing or measuring circuitry and/or an evaluation circuitry and/or an I/O circuitry. Of course, one or more of these circuitry may also be contained in a semiconductor chip 30 of the aforementioned embodiments.

The solder deposits 26 may be used to electrically couple the device 200 to other components, see FIG. 9.

FIGS. 8A to 8E schematically illustrate one embodiment of a method to produce a semiconductor device 200. The method steps shown in FIGS. 8A and 8B correspond to the method steps in FIGS. 7A and 7B, and reference is made to the corresponding description.

According to FIG. 8C, the plastic material 3 is deposited on the continuous (i.e., unstructured) graphene layer 2. Deposition of the plastic material 3 may be accomplished in the same way as described in conjunction with FIG. 7D.

According to FIG. 8D, the graphene layer 2 is structured. In this embodiment the plastic material 3 (also referred to as a glob top material in the art) is used as a mask for structuring the graphene layer 3. That is, the regions of the graphene layer 2, which are not covered by the plastic material 3, may be removed by a solvent or etching agent. By way of example, an $O_2$-plasma etching process may be used. As a result, the design or pattern of the remaining portions of the graphene layer 2 is in conformity to the design or pattern of the plastic material 3 (FIG. 8D). The provision of the plastic material 3 as a mask for structuring the graphene layer 2 guarantees that the graphene layer 2 is completely covered and sealed by the plastic material 3.

As illustrated in FIG. 8E, the semiconductor wafer 20 may then be singulated into semiconductor chips 30. This method step is analogous to the method step illustrated in FIG. 7E, and reference is made to the accompanying description in order to avoid reiteration.

FIG. 9 illustrates a cross-sectional view of sensor device 200 mounted on a carrier 40 such as, e.g., a PCB (Printed Circuit Board). Here, by way of example, the sensor device 200 is mounted on the carrier 40 in a flip-chip orientation. The sensor device 200 is the finished sensor device, and is also referred to as a wafer level package in the art.

Figure 10A:
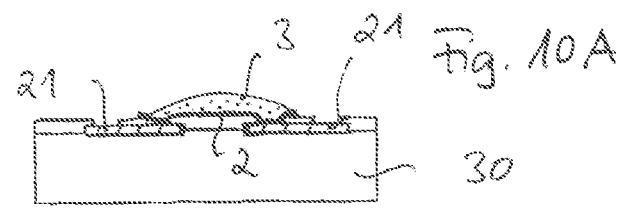
Figure 10B:
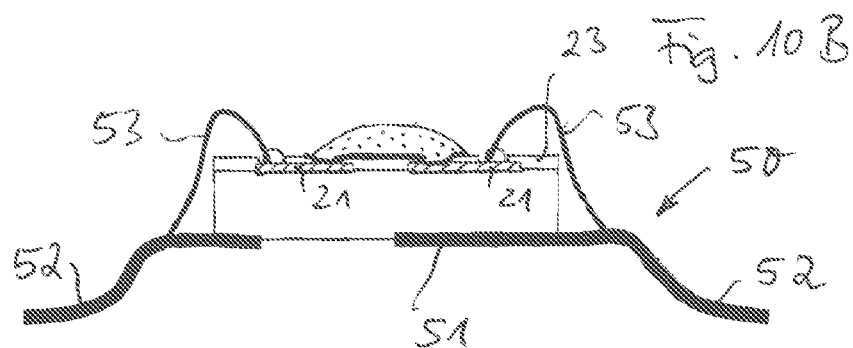

FIGS. 10A to 10D illustrate one embodiment of a method to produce a sensor device 300, a cross-section of which is illustrated in FIG. 10D. In order to manufacture the sensor device 300, a leadframe 50 may be provided which is illustrated in FIG. 10B in cross-section. The leadframe 50 may include one or more die pads 51 and a plurality of leads 52. The leadframe 50 may be manufactured from a metal or metal alloy, in particular copper, a copper alloy, iron, nickel, aluminum, or other appropriate materials. Furthermore, the leadframe 50 may be plated with an electrically conductive material, for example, copper, silver, iron, nickel or nickel phosphorus. The shape of the leadframe 50 is not limited to any size or geometric shape. The leadframe 50 may have been manufactured by punching a metal plate.

As illustrated in FIG. 10B, the semiconductor chip 30 (FIG. 10A) is placed over the die pad 51. In the present embodiment the semiconductor chip 30 is mounted on the die pad 51 with the chip electrodes 21 facing away from the die pad 51. The semiconductor chip 30 may be attached to the die pad 51 by using an appropriate adhesive material.

It is to be noted that the semiconductor chip 30 may be produced by any of the aforementioned methods. In particular, the semiconductor chip 30 may be manufactured by one of the methods illustrated in FIGS. 7A to 7E and FIGS. 8A to 8E, with the step of attaching the solder deposits 26 being omitted.

As illustrated further in FIG. 10B, the chip electrodes 21 may be connected to lead 52 of the leadframe 50 by wire-bonding. In wire-bonding the tip of a bond-wire 53 is pressed by wire-bonding tool against the chip electrode 21 of the semiconductor chip 30 and heat and/or ultrasonic energy is applied to create a metallic connection. The wire-bonding tool next extends the wire 53 to a bonding pad on the leadframe 50 and makes a "stitch" bond to that pad.

Figure 10C:
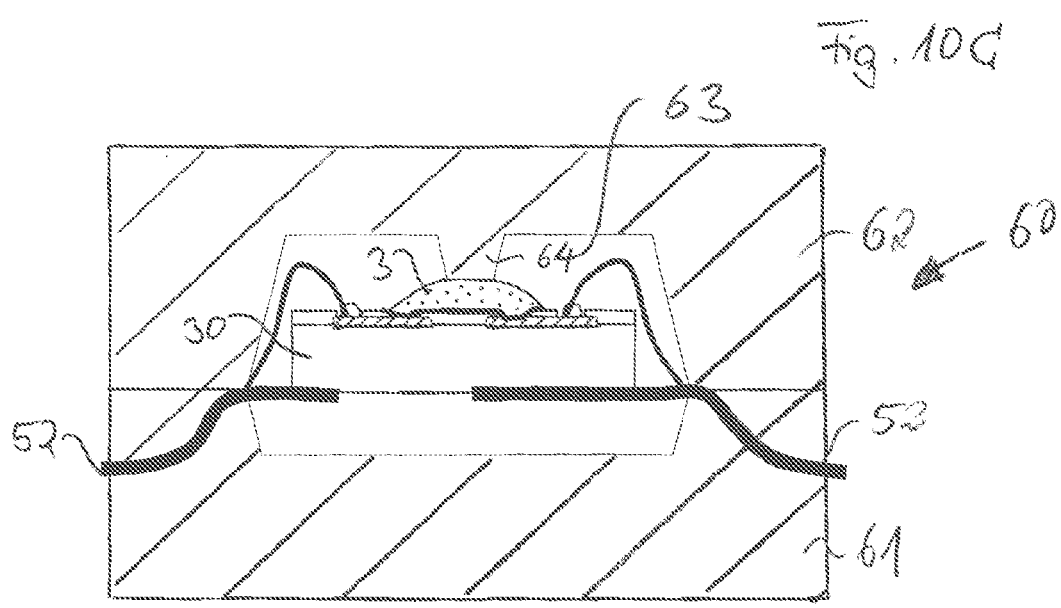

As illustrated in FIG. 10C, the wire-bonded structure shown in FIG. 10B may be placed in a mold tool 60. The mold tool 60 may comprise a lower half 61 and an upper half 62. The lower half 61 and the upper half 62 are brought together and closed, with the halves 61 and 62 defining a cavity 63 in which the structure shown in FIG. 10B is accommodated. The upper half 62 may have a dome or post 64 which is pressed on the top surface of the plastic material 3. Except the abutment of the dome or post 64 onto the top surface of the plastic material 3 and the lead 52 of the leadframe 50 fixed by the mold tool, the structure shown in FIG. 10A may have no peripheral areas which are in contact to walls of the cavity 63. Thus, the semiconductor chip 30, the insulating layer 23, the chip electrodes 21, exposed parts of the graphene layer 2, if any, and the plastic material 3 are completely over-molded by the encapsulating material introduced into the cavity 63. This process may be accompanied by the application of heat and pressure. After curing, the encapsulating material is rigid and forms an encapsulation body 65 (FIG. 10D). The encapsulation body 65 has an opening 17 conforming to the shape of the post or dome 64 of the upper mold half 62, with the opening 17 exposing a central part of the plastic material 3. The opening 17 may have lateral dimensions which are equal or smaller than the distance between the chip electrodes 21. As illustrated in FIG. 10D, the encapsulation body 65 may also completely cover the bottom of the semiconductor chip 30 and the side faces of the semiconductor chip 30. Thus, the semiconductor chip 30 may be hermetically sealed by the encapsulation body 65 and the plastic material 3 and the leads 52 are the only members of the structure shown in FIG. 10B which are exposed by or protrude out of the encapsulation body 65.

As illustrated in FIG. 11, the structure shown in FIG. 10A may also be mounted on a leadframe 50 in a flip-chip orientation. To that end, the structure shown in FIG. 10A is equipped with solder deposits 26 to form a device similar to the sensor device 200 as illustrated in FIG. 7E. The sensor device 200 is then mounted on the leadframe 50, e.g., by a solder reflow process. Subsequently, the sensor device 200 mounted on the leadframe 50 is placed in a mold tool for fabricating the encapsulation body 67. The molding tool is similar to the molding tool 60 as shown in FIG. 10C, with the exception that the dome or post 64 forms part of the lower mold half 61 rather than the upper mold half 62 and passes an opening between leads 52 of the leadframe 50. The manufacturing process of the sensor device 400 illustrated in FIG. 11 may be identical to the manufacturing process explained above in conjunction with FIGS. 10A to 10D. Further, similar to the sensor device 300 illustrated in FIG. 10D, the encapsulation body 67 of the sensor device 400 may completely encapsulate the chip 30, the chip electrodes 21, the insulating layer 23, the graphene layer 2 (if not yet covered by the plastic material 3) and the plastic material 3 except a central surface portion thereof. Again, the dimension of the opening 17 of the encapsulation body to expose the central portion of the plastic material 3 may be equal or smaller than the distance between the chip electrodes 21.

FIG. 12 illustrates one embodiment of a sensor device 500 in a cross-sectional view. The sensor device 500 uses a leadless package such as, e.g., a so-called TSLP (Thin Small Leadless Package). Such type of package may comprise a carrier containing a metal chip pad 502 and metal contact pads 503, 504 spaced apart and electrically insulated to each other by polymer material 505. Compared to conventional leadframe techniques, in which leads or contact pads are typically structured by punching or etching, the structuring method used in leadless packages allows for a considerably higher packaging density. Further, the design variability is enhanced, because the pads 502, 503, 504 may be insular, whereas in conventional leadframe technique, each contact pad or lead has to be suspended at the frame structure of the leadframe.

A structured insulating layer 510 may extend on the carrier 502, 503, 504, 505 and may cover zones between the chip pad 502 and the contact pads 503, 504. The structured insulating layer 510 may be used as a supporting basis for conducting lines 511 electrically connecting to the contact pads 503, 504, the graphene layer 2 and, possibly, to chip electrodes (not illustrated). The arrangement of the graphene layer 2 and the plastic material 3 is similar to embodiments described before and will be omitted for the sake of brevity.

FIGS. 13A to 13M schematically illustrate a method of manufacturing a sensor device 600, a cross-section of which is shown in FIG. 15. The method shown in FIGS. 13A to 13M is an implementation of the method shown in FIGS. 1A to 1C. The details of the production method, that are described below, can therefore be likewise applied to the method of FIGS. 1A to 1C. Vice versa, the description of the processing steps described in conjunction with FIGS. 1A to 1C may be applied to the method explained below with reference to FIGS. 13A to 13M.

Figure 13A:
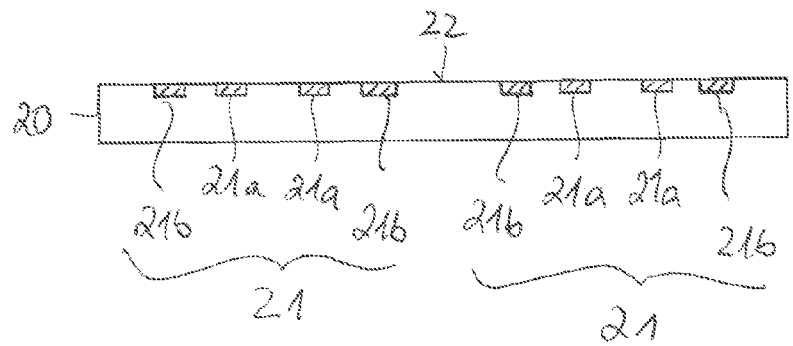

As illustrated in FIG. 13A, a semiconductor wafer may include a bulk silicon in which integrated circuits are embedded. Chip electrodes 21 may comprise first chip electrodes 21a and second chip electrodes 21b. The chip electrodes 21a and 21b may be made of metal, for example, aluminum or copper or any other metal mentioned above with reference to chip electrode 21.

Figure 13B:
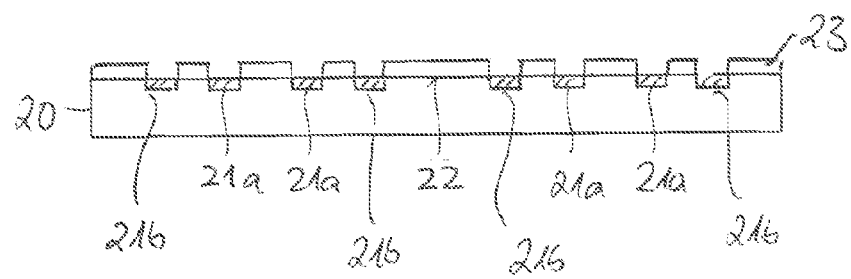

According to FIG. 13B, an insulating layer 23 is deposited on the first main face 22 of the wafer 20. The insulating layer 23 may, for example, be made of the same materials as mentioned above with reference to other embodiments. Thus, in particular, the insulating layer 23 may be a polymer layer or a hard passivation layer or a layer composed of a lower hard passivation layer and an upper polymer layer.

As illustrated in FIG. 13B, the insulating layer 23 is structured to expose the first chip electrodes 21a and the second chip electrodes 21b. All method steps mentioned before to structure the insulating layer 23 may be applied.

Figure 13C:
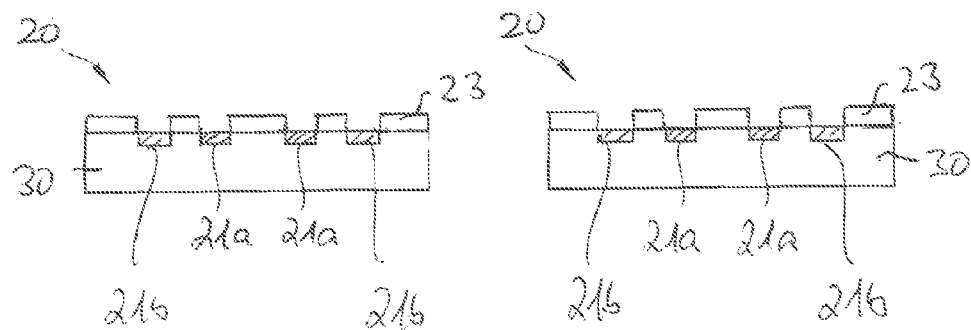

As illustrated in FIG. 13C, the semiconductor wafer 20 may then be singulated into the semiconductor chips 30, for example, by sawing, cutting, etching or laser ablation.

In order to package the semiconductor chips 30, a temporary carrier 80 is provided as illustrated in FIG. 13D. The temporary carrier 80 may be a plate of a rigid material, for example, a metal, such as nickel, steel or stainless steel, laminate, film or a material stack. The temporary carrier 80 may have at least one flat surface on which the semiconductor chips 30 may be placed. An adhesive tape 81, for example, a double-sided sticky tape, may be laminated on the temporary carrier 80.

As illustrated in FIG. 13E, the semiconductor chips 30 are mounted on the temporary carrier 80. The semiconductor chips 30 can be fixed on the adhesive tape 81. For attaching the semiconductor chips 30 to the temporary carrier 80, other kinds of attaching materials or devices such as, e.g., vacuum holders may alternatively be used.

As shown in FIG. 14, the semiconductor chips 30 may be arranged in an array, with the semiconductor chips 30 being spaced apart from each other in a certain distance. The temporary carrier 80 may be round (see FIG. 14) or square shaped. The temporary carrier 80 may have any appropriate size, e.g., a diameter D of about 0.2 or 0.3 m or more.

Referring again to FIG. 13E, the semiconductor chips 30 may be arranged over the temporary carrier 80 with their first main faces 22 containing the first and second chip electrodes 21a, 21b facing the temporary carrier 80. In this case, the insulating layer 23 may be in direct contact with the adhesive tape 81.

After the semiconductor chips 30 have been mounted on the temporary carrier 80, they are encapsulated with an encapsulating material forming an encapsulation body 90 as illustrated in FIG. 13F. The encapsulating material may cover second main faces 29 of the semiconductor chips 30, which are opposite to the first main faces 22, and also the side faces 28 of the semiconductor chips 30. The gaps between the semiconductor chips 30 are also filled with the encapsulating material. For example, the encapsulating material may be a duroplastic or film resetting mold material. The encapsulating material may be based on an epoxy material and may contain a filling material consisting of small particles of glass ($SiO_2$) or other electrically insulating mineral filler materials like $Al_2O_3$ or organic filler materials. The mold material may, for example, be applied by compression molding, injection molding, granulate molding, powder molding or liquid molding. The encapsulation body 90 embedding the semiconductor chips 30 is also referred to as artificial wafer in the art.

Alternatively, the encapsulating material may be a polymer material having the shape of an electrically insulating foil or sheet, which is laminated on top of the semiconductor chips 30 as well as the temporary carrier 80. Also in this case the gaps between the semiconductor chips 30 are filled with the polymer material. The polymer material may, for example, be a prepreg (short for pre-impregnated fibers) that is a combination of a fiber mat, for example, glass or carbon-fibers, and a resin, for example, a duroplastic material. For the lamination of a prepreg the same or similar process steps can be used as in PCB manufacturing.

The semiconductor chips 30 encapsulated in the encapsulation body 90 are then released from the temporary carrier 80, and the adhesive tape 81 is peeled from the encapsulating material and the insulating layer 23 as illustrated in FIG. 13G. The adhesive tape 81 may feature thermo-release properties, which allow for the removal of the adhesive tape 81 during a heat treatment. The removal of the adhesive tape 81 from the temporary carrier 80 is carried out at an appropriate temperature, which depends on the thermo-release properties of the adhesive tape 81 and is usually higher than 150° C.

After the release of the temporary carrier 80 and the adhesive tape 81, the face of the insulating layer 23 facing away from the semiconductor chip 30 and the bottom surface of the encapsulation body 90 form a substantially common plane P. As described below and illustrated in FIGS. 13H to 13K, a redistribution layer may be applied to the plane P.

A dielectric layer 91 may be deposited on the plane P as illustrated in FIG. 13H. The dielectric layer 91 may be fabricated in various ways. For example, the dielectric layer 91 may be deposited from a gas phase or from a solution, or can be laminated onto the surface of the plane P. Furthermore, thin-filmed technology methods may be used for the application of the dielectric layer 91. The dielectric layer 91 may be fabricated from a polymer such as, e.g., parylene, photoresist material, imide, epoxy, duroplast, silicone, silicone nitride or an inorganic, ceramic-like material such as silicon-carbon compounds. The dielectric layer 91 may also be omitted.

In order to make electrical contacts to the integrated circuits embedded in the semiconductor chips 30, the dielectric layer 91 may be opened in areas where the first and second chip electrodes 21a, 21b are arranged as illustrated in FIG. 13H. The openings 92 in the dielectric layer 91 may, for example, be produced by using photolithographic methods and/or etching methods.

A metal layer 93 may be applied to the dielectric layer 91 and is structured as illustrated in FIG. 13I. According to one embodiment, the metal layer 93 may be fabricated by a plating process. By way of example, in a first step, a seed layer (not shown) may be deposited on the dielectric layer 91 and may be covered by a photoresist layer (not shown) structured by a photo-lithographic process. Subsequently the portion of the seed layer exposed by the photoresist layer may be reinforced by galvanic deposition of a metallic material. During the galvanic deposition of the metallic material the seed layer is employed as an electrode. Copper or other metals or metal alloys may be plated on the seed layer in the unmasked areas and to the desired height, which is usually greater than 3 μm. That way, metal electrodes 93a and conductor traces 93b may be fabricated. In the embodiment illustrated in FIG. 13I the metal electrodes 93a electrically connect to the first chip electrodes 21a and the conductor traces 93b electrically connect to the second chip electrodes 21b.

According to FIG. 13J, a dielectric layer 94 may be deposited on top of the metal layer 93. The dielectric layer 94 may be opened in certain areas to expose portions of the metal electrodes 93a and portions of the conductor traces 93b. The exposed portions of the conductor traces 93b serve as external contact pads. The exposed portions of the metal electrodes 93a serve as electrical contacts for the graphene layer 2 to be electrically connected thereto. The dielectric layer 94 may be produced by using the same or similar materials and processing steps as described above in connection with the dielectric layer 91.

As illustrated in FIG. 13K, a structured graphene layer 2 is generated to extend between the at least two electrical contacts formed by the exposed portions of the metal electrodes 93a associated with one semiconductor chip 30. The graphene layer 2 may be deposited and structured by using the same or similar materials and processing steps as described above in connection with previous embodiments. The structured graphene layer 2 may directly overlay the dielectric layer 94 in its peripheral region, may directly overlay the dielectric layer 91 in its central region and may directly connect to the metal electrodes 93a in a region between the peripheral region and the central region.

As illustrated in FIG. 13L, the plastic material 3 is then deposited on the graphene layer 2. The plastic material 3 may be deposited and structured by using the same or similar materials and processing steps as described above in connection with the foregoing embodiments. In particular, the plastic material 3 may either be deposited on a pre-structured graphene layer 2 in accordance with the embodiments illustrated in FIGS. 7A to 7E or the plastic material 3 may be deposited on the unstructured graphene layer 2 and utilized as a mask to structure the graphene layer 2 as described in the embodiment of FIGS. 8A to 8E.

Solder deposits 26 may be placed on external contact pads provided by the exposed portions of the conductor traces 93b as illustrated in FIG. 13M. The solder deposits 26 may be applied by so-called "ball placement" or other methods such as, e.g., stencil printing followed by a heat-treatment process. The solder deposits 26 may, for example, be made of the materials mentioned before and may be used to electrically couple the device 600 illustrated in FIG. 15 to other components, for example, a PCB.

As illustrated in FIG. 13M by the dashed separation line, the devices 600 are separated from one another by separation of the encapsulation body 90 and possibly the redistribution structure of layers 91, 93, 94, for example, by sawing, cutting, etching or a laser beam.

The sensor devices 600 (FIG. 15) manufactured by the method described above is the finished sensor device, and is also referred to as an embedded wafer level package in the art. Such packages may be fan-out type packages. That is, the encapsulation body 90 allows the redistribution layer to extend beyond the outline of the semiconductor chip 30. The solder deposits 26 therefore do not need to be arranged within the outline of the semiconductor chips 30, but can be distributed over a larger area. The increased area, which is available for arrangement of the solder deposits 26, means that the solder deposits 26 may be arranged at a greater distance from one another and/or the maximum number of solder deposits 26 can be increased compared to the situation when all the solder deposits 26 are arranged within the outline of the semiconductor chips 30. By increasing the number of external terminals (e.g., solder deposits 26) of the sensor device 600, the functionality and performance of the sensor device 600 may be enhanced. By way of example, the integrated circuit in the semiconductor chip 30 may be configured to have enhanced functionality such as processor functionality, logic functionality, memory functionality, etc.

The sensor devices of all embodiments described herein may be used, e.g., for the detection of fluids such as gases or liquids, in particular nitrogen oxide, carbon dioxide, carbon monoxide, hydrogen sulfite, methane, etc. Further, all these sensor devices may be used, e.g., as indoor-air-quality sensors, sensors for controlling a combustion engine, explosive agent detectors, selective fire detectors, etc.

In addition, while a particular feature or aspect of an embodiment of the invention may have been disclosed with respect to only one of several implementations, such feature or aspect may be combined with one or more other features or aspects of the other implementations as may be desired and advantageous for any given or particular application. Furthermore, to the extent that the terms "include", "have", "with", or other variants thereof are used in either the detailed description or the claims, such terms are intended to be inclusive in a manner similar to the term "comprise". Furthermore, it should be understood that embodiments of the invention may be implemented in discrete circuits, partially integrated circuits or fully integrated circuits or programming means. Also, the term "exemplary" is merely meant as an example, rather than the best or optimal. It is also to be appreciated that features and/or elements depicted herein are illustrated with particular dimensions relative to one another for purposes of simplicity and ease of understanding, and that actual dimensions may differ substantially from that illustrated herein.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A sensor device comprising:
a semiconductor chip;
a graphene layer disposed over the semiconductor chip;
electrical contacts coupled to the graphene layer; and
a sensor housing that accommodates the semiconductor chip and the graphene layer, wherein the sensor housing comprises an opening located above the graphene layer.

2. The sensor device of claim 1, further comprising a plastic material disposed over the graphene layer, wherein the opening exposes the plastic material.

3. The sensor device of claim 2, wherein the plastic material is partially disposed over the graphene layer.

4. The sensor device of claim 2, wherein the plastic material comprises polyethylenterephtalate.

5. The sensor device of claim 2, wherein the plastic material comprises polyvinylidene.

6. The sensor device of claim 2, further comprising a polymer foil disposed over the plastic material, wherein the polymer foil comprises an opening exposing the plastic material.

7. The sensor device of claim 1, wherein the sensor housing comprises a molded encapsulating material.

8. The sensor device of claim 1, wherein the sensor housing is a hollow housing.

9. The sensor device of claim 1, wherein the opening has lateral dimensions which are equal or smaller than a distance between the electrical contacts.

10. The sensor device of claim 1, wherein the semiconductor chip comprises an integrated circuit configured to measure an electrical resistance between the electrical contacts coupled to the graphene layer.

11. An arrangement comprising:
a carrier comprising carrier contacts; and
a sensor device comprising:
a semiconductor chip;
a graphene layer disposed over the semiconductor chip;
electrical contacts coupled to the graphene layer; and
a sensor housing that accommodates the semiconductor chip and the graphene layer, wherein the sensor housing comprises an opening located vertically above the graphene layer, and wherein the electrical contacts of the sensor device are electrically connected to the carrier contacts of the carrier.

12. The arrangement of claim 11, wherein the sensor device further comprises a plastic material disposed over the graphene layer, wherein the opening exposes the plastic material.

13. The arrangement of claim 12, wherein the plastic material is partially disposed over the graphene layer.

14. The arrangement of claim 11, wherein the opening has lateral dimensions which are equal or smaller than a distance between the electrical contacts.

15. The arrangement of claim 11, wherein the carrier is a printed circuit board (PCB).

16. The arrangement of claim 11, wherein the semiconductor chip comprises an integrated circuit.

17. An arrangement comprising:
a leadframe; and
a sensor device comprising:
a semiconductor chip;
a graphene layer disposed over the semiconductor chip;
electrical contacts coupled to the graphene layer; and
a housing that accommodates the semiconductor chip and the graphene layer, wherein the housing comprises an opening located above the graphene layer, and wherein the electrical contacts of the sensor device are electrically connected to the leadframe.

18. The arrangement of claim 17, wherein the sensor device further comprises a plastic material disposed over the graphene layer, wherein the opening exposes the plastic material.

19. The arrangement of claim 17, wherein the electrical contacts of the sensor device are electrically connected to the leadframe via bond wires.

20. The arrangement of claim 17, wherein the housing further accommodates a portion of the leadframe.

21. The arrangement of claim 17, wherein the housing comprises a molded encapsulating material.

22. The arrangement of claim 17, wherein the semiconductor chip comprises an integrated circuit.

23. A leadless package comprising:
a metal chip pad, a first metal contact and a second metal contact disposed in a bottom surface of the leadless package;
a semiconductor chip disposed on the metal chip pad;
a first electrical contact and a second electrical contact disposed at a top surface of the semiconductor chip, wherein the semiconductor chip comprises an integrated circuit configured to measure an empirical parameter between the first electrical contact and the second electrical contact;
a first metal layer connection and a second metal layer connection, wherein the first metal layer connection connects the first electrical contact to the first metal contact, and wherein the second metal layer connection connects the second electrical contact to the second metal contact; and
a graphene layer disposed over the semiconductor chip, wherein the graphene layer connects the first electrical contact and the second electrical contact.

24. The leadless package of claim 23, further comprising a plastic material disposed over the graphene layer, wherein the plastic material completely covers the graphene layer.

25. The leadless package of claim 24, wherein the plastic material comprises at least one of a polyethylenterephtalate and polyvinylidene.

26. A sensor device comprising:
an encapsulation body;
a semiconductor chip disposed in the encapsulation body;
a redistribution layer disposed on the semiconductor chip and the encapsulation body, wherein a first trace of the redistribution layer connects a first chip electrical contact to a first contact terminal on a first area of the encapsulation body, and wherein a second trace of the redistribution layer connects a second chip electrical contact to a second contact terminal on a second area of the encapsulation body; and
a graphene layer disposed over the semiconductor chip and connected to a third chip electrical contact and a fourth chip electrical contact, wherein the encapsulation body comprises an opening located above the graphene layer.

27. The sensor device of claim 26, wherein a plastic material is disposed over the graphene layer, wherein the opening exposes the plastic material.

28. The sensor device of claim 27, wherein the plastic material completely covers the graphene layer.

29. The sensor device of claim 26, wherein the opening has lateral dimensions which are equal to or smaller than a distance between the third chip electrical contact and the fourth chip electrical contact.

* * * * *